United States Patent
Gomez et al.

(10) Patent No.: US 8,333,741 B2
(45) Date of Patent: Dec. 18, 2012

(54) PHACOEMULSIFICATION CANNULA WITH IMPROVED PURCHASE

(75) Inventors: Mario P. Gomez, St. Louis, MO (US); Iidefonso Gonzalez, St. Charles, MO (US); Dimas Joel Rullan, St. Charles, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 1501 days.

(21) Appl. No.: 11/595,545

(22) Filed: Nov. 10, 2006

(65) Prior Publication Data

US 2008/0114313 A1 May 15, 2008

(51) Int. Cl.
*A61M 35/00* (2006.01)

(52) U.S. Cl. ....................................................... 604/294

(58) Field of Classification Search .................... 604/294
See application file for complete search history.

(56) References Cited

U.S. PATENT DOCUMENTS

| | | | | |
|---|---|---|---|---|
| 3,386,438 A | * | 6/1968 | Stevens | 604/272 |
| 3,527,217 A | * | 9/1970 | Gettig | 604/243 |
| 4,816,018 A | * | 3/1989 | Parisi | 604/22 |
| 5,464,389 A | | 11/1995 | Stahl | |
| 5,759,179 A | * | 6/1998 | Balbierz | 604/272 |
| 5,989,209 A | * | 11/1999 | Barrett | 604/22 |
| 6,159,175 A | * | 12/2000 | Strukel et al. | 604/22 |
| 6,350,251 B1 | * | 2/2002 | Prosl et al. | 604/93.01 |
| 6,629,959 B2 | * | 10/2003 | Kuracina et al. | 604/192 |
| 7,204,820 B2 | * | 4/2007 | Akahoshi | 604/22 |
| 7,299,707 B1 | * | 11/2007 | Evans | 73/861.63 |
| 7,588,553 B2 | * | 9/2009 | Dewey | 604/22 |
| 2001/0031951 A1 | * | 10/2001 | Pezzola | 604/275 |
| 2004/0039351 A1 | * | 2/2004 | Barrett | 604/272 |
| 2005/0059939 A1 | | 3/2005 | Perkins et al. | 604/272 |

FOREIGN PATENT DOCUMENTS

| | | |
|---|---|---|
| EP | 0 342 448 | 11/1989 |
| EP | 1 129 681 | 9/2001 |
| WO | WO96/38091 | * 12/1996 |

* cited by examiner

*Primary Examiner* — Tatyana Zalukaeva
*Assistant Examiner* — Ginger T Chapman
(74) *Attorney, Agent, or Firm* — Jeffrey B. Powers

(57) ABSTRACT

A phacoemulsification cannula 10 includes a hub 12 for engagement with an ophthalmic surgical instrument. An elongated needle 14 having a proximal end 16 is attached to the hub 12. The cannula 10 has an aspiration lumen 20 spanning a majority of a length of a needle 14 from the proximal end towards a distal end 18. A venturi lumen 22 is formed in the needle adjacent the distal end. The venturi lumen 22 is in communication with the aspiration lumen 20 so that fluid and tissue may be aspirated through the venturi lumen 22 and the aspiration lumen 20.

6 Claims, 3 Drawing Sheets

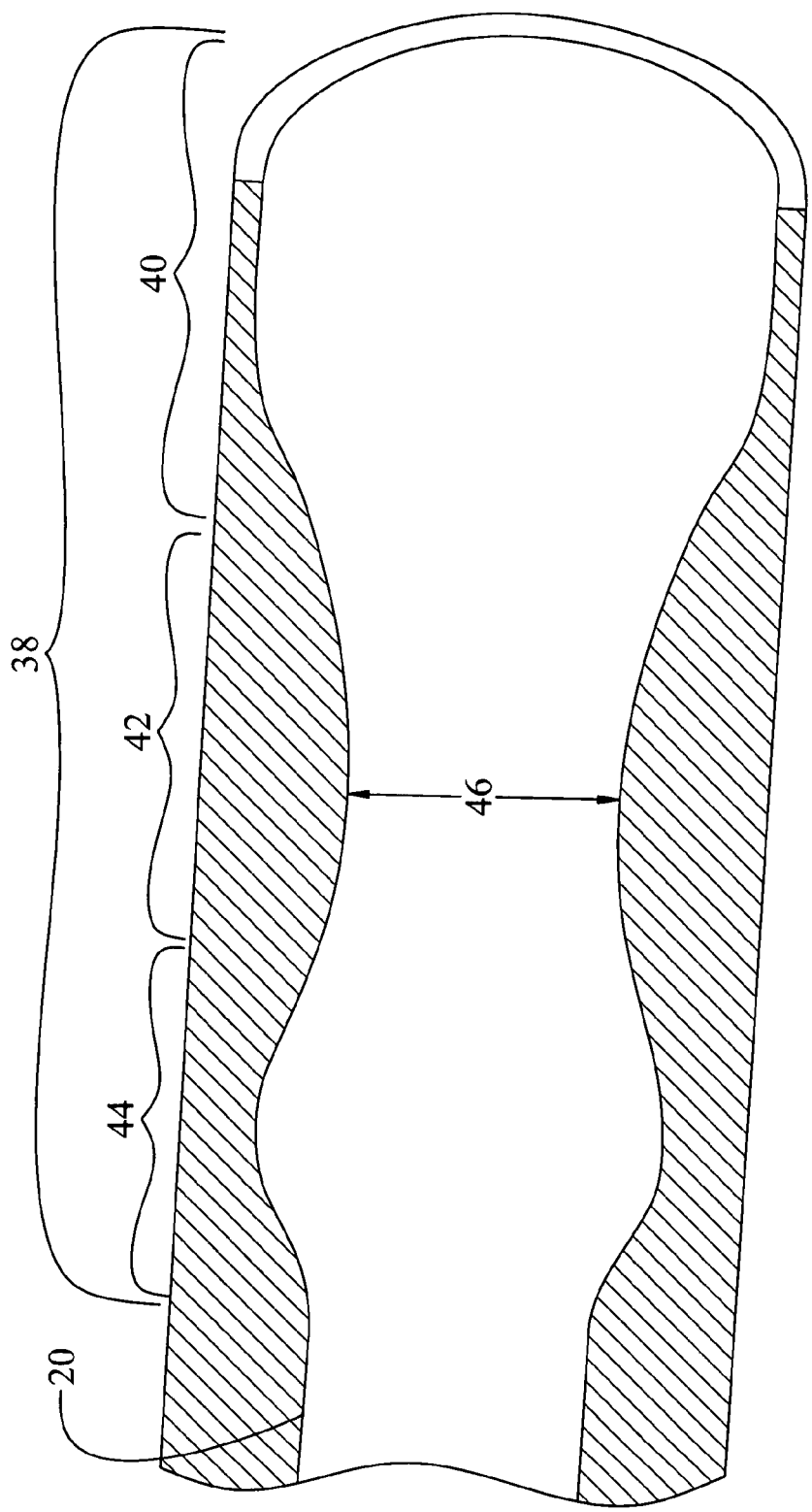

PHACOEMULSIFICATION CANNULA WITH IMPROVED PURCHASE

BACKGROUND OF THE INVENTION

1. Field of the Invention

The present is related to phacoemulsification needles or cannulas for use in ophthalmic surgery, especially cataract surgery. More particularly, the present invention is directed to a phacoemulsification cannula with improved purchase or suction at the distal end of the cannula.

2. Description of Related Art

The use of phacoemulsification cannulas in ophthalmic surgery and especially in cataract surgery is well known. Typical cannulas include an inner lumen through which fluids and tissue are aspirated away from a patient's eye, through the lumen of the aspiration needle, and eventually to a collection bag or cassette. The purpose of the phacoemulsification cannula is to transfer ultrasonic energy from a phacoemulsification handpiece in order to break-up cataracts in the eye and then aspirate fluids and the cataract tissue through the lumen of the cannula.

There have been many phacoemulsification cannula designs which typically are directed towards improving the break-up of cataract tissue in order to make the surgery more time efficient. Such designs include having angled tips and having bores within the tip that transition from a larger diameter to a smaller diameter. In addition, these larger bores at the distal end of the phacoemulsification needles typically are either stepped in their transition or tapered. Each of these prior art needles or cannulas has been designed to more efficiently break-up cataract tissue once it has been sucked within the cannula lumen. Because of the longitudinal in and out or jack hammer-like motion of the phaco needle during the use of ultrasonic energy, it is often difficult for the phacoemulsification cannula to make significant contact with the cataract. This is because as the cannula moves out away from the handpiece and towards the cataract, the cannula effectively pushes the cataract away. A surgeon relies on the vacuum or suction force of the surgical system that is asserted through the lumen of the cannula to hold or purchase the cataract to the cannula. In order to provide greater purchase of the cannula, the aspiration levels need to be increased. Such an increase in aspiration levels can cause significant dangers and problems in surgery, such as a surge of fluid into the cannula after an occlusion of the cannula has been cleared. This post-occlusion surge can cause the collapse of the eye resulting in damage to delicate tissues in the eye and in serious damage to the eye.

Therefore, it would be desirable to provide a phacoemulsification cannula with increased purchase as compared to the prior art without the need to significant increase the aspiration levels applied through the cannula's lumen.

BRIEF DESCRIPTION OF THE DRAWINGS

FIG. 3 is an alternate embodiment of FIG. 2 in accordance with the present invention.

DETAILED DESCRIPTION OF THE PREFERRED EMBODIMENT

Figure 1:
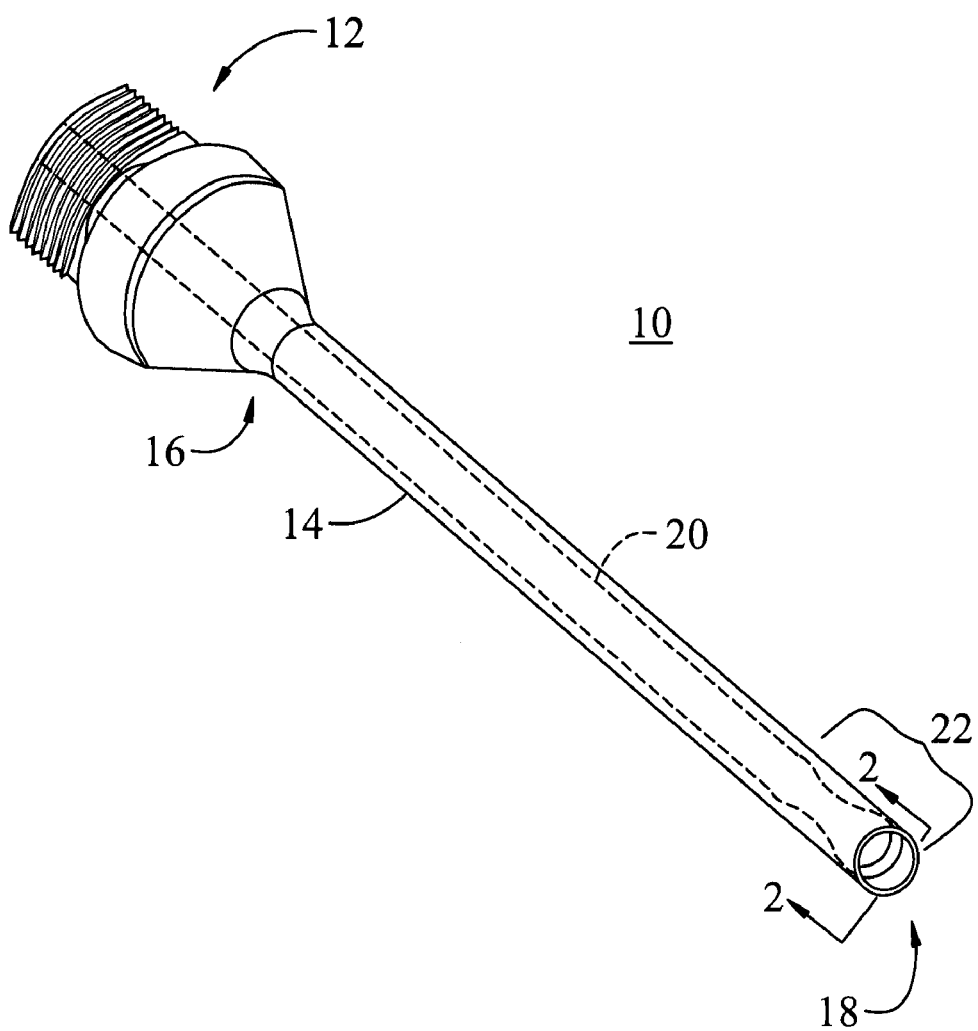
FIG. 1 is a perspective view of a phacoemulsification cannula in accordance with the present invention.

FIG. 1 shows a phacoemulsification cannula 10 for use in ophthalmic surgery. Cannula 10 includes a hub 12 for engagement with an ophthalmic surgical instrument (not shown), such as an ultrasonic handpiece for vibrating cannula 10 during cataract surgery. Those skilled in the art will appreciate that cannula 10 may also be attached to other devices such as an irrigation/aspiration handpiece. Cannula 10 further includes an elongated needle 14 having a proximal end 16 attached to the hub 12 and a distal end 18. The cannula 10 has an aspiration lumen 20 shown as dashed lines in FIG. 1. Lumen 20 spans a majority of a length of needle 14 and has a first diameter which is essentially constant from the proximal end 16 towards the distal end 18. A venturi lumen, shown generally at 22, is in communication with the aspiration lumen 20 as shown, so that fluid and tissue may be aspirated through the venturi lumen and the aspiration lumen 20.

As is shown, hub 12 is preferably threaded so that the cannula 10 may be attached to a standard ultrasonic handpiece. Though other hub configurations and attachment mechanisms may be used.

As can be seen, venturi lumen 22 has a generally hour-glass shape, such that the venturi lumen 22 includes structure creating a double venturi. That is to say that the venturi lumen at the tip of distal end 18 transitions from a large diameter to a small diameter and then back out towards a larger diameter before transitioning to lumen 20.

Figure 2:
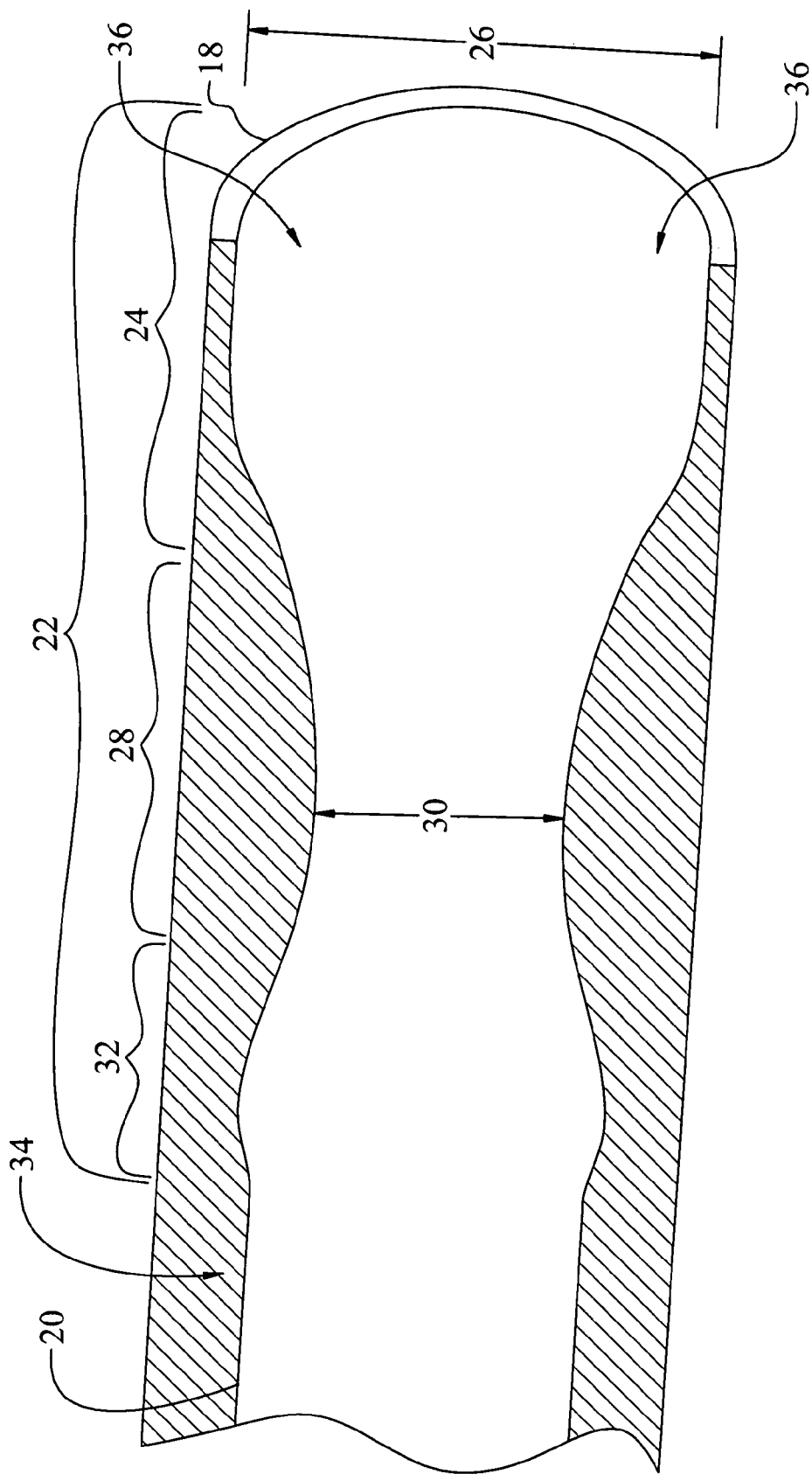
FIG. 2 is a partial cut away of FIG. 1 taken along line 2-2.

FIG. 2 shows a partial cut away elevation of FIG. 1 along line 2-2. As can be seen, the venturi lumen 22 includes a first venturi section 24 having a maximum diameter 26, a second venturi section 28 having a minimum diameter 30, and a third venturi section 32 at a place shown generally at 34 connecting the aspiration lumen 20 to the venturi lumen 22. As can be seen, the venturi lumen 22 includes structure forming smoothly varying transitions between each of the first, second, and third venturi sections 24, 28, and 32, respectively. As those skilled in the art will appreciate, such smoothly varying transitions are important to promote non-turbulent laminar flow into the venturi lumen 22.

As fluid and debris are pulled within venturi lumen 22, as indicated by arrows 36, the transition to minimum diameter 30 causes the fluid to increase in speed which causes a significant increase in the suction power at the distal end 18. By placing the venturi lumen 22 as near as possible to the distal end 18, a significant increase in suction power at a given aspiration level is achieved as compared to prior art phacoemulsification cannulas that have either a straight, stepped, or tapered bore at the distal end. In fact, depending on the construction of the prior art phacoemulsification cannulas, prior art cannulas may actually have a somewhat adverse effect on the suction at the cannula's tip rather than the increased suction of the present invention. These pressure losses at the tips of the prior art cannulas, may also be referred to as vena contracta. If the shape of the internal lumen presents abrupt changes in diameter the flow of fluid will be disrupted and may actually work to repel the inflow of tissue. It is important that the venturi lumen be placed as near the distal end 18 as possible so that the increased fluid velocity and resulting suction can be utilized for fluids and tissue outside of the cannula 10.

In modeling the present inventive venturi cannula in comparison to a prior art phacoemulsification cannula, it was found that the purchase or suction of the present invention was at least four (4) times greater than the prior art cannula and it is believed that the purchase may be much greater compared to some other prior art cannulas. The prior art cannula had a profile that generated approximately 0.8 meters-per-second velocity at the distal end of the cannula compared to the present invention which generated approximately 2.1 meters-per-second velocity of fluid at the distal tip.

According to Bernoulli's Laws of Fluid Mechanics, the force resulting from the pressure generated by a fluid flow is proportional to the square of the velocity. Therefore, the present invention creates a significantly higher holding force than the prior art cannula to which it was compared.

FIG. 3 shows an alternate embodiment in accordance with the present invention of a venturi lumen. Venturi lumen 38 is essentially the same as venturi lumen 22 described above and includes venturi lumen sections 40, 42, and 44, which are essentially the same as venturi lumen sections 24, 28, and 32, described above. FIG. 3 is different from FIG. 2 in that the minimum diameter 46 of venturi lumen section 42 is approximately equal to the diameter of aspiration lumen 20. Another embodiment not shown includes a venturi lumen without the third venturi section, but instead smoothly transitions from the minimum diameter to a diameter equal to the aspiration lumen 20. Aspiration lumen 20 should preferably not be smaller than the minimum diameter of the venturi lumen to prevent particles from clogging the phacoemulsification cannula. In FIG. 2, the third venturi section has a largest diameter that is greater than the minimum diameter 30 and is greater than the first diameter of aspiration lumen 20 and is equal to or less than the maximum diameter of the first venturi section 24.

The terms first venturi section, second venturi section, and third venturi section are not to be construed as to be referring to a specific place within the venturi lumen or within the cannula 10, but rather are terms to describe the shape of the venturi lumen. As mentioned above, each section smoothly transitions from one section to another and therefore, there is no specific place where one section stops and another section begins. The venturi section terms have been used as a convenient way to describe the venturi lumen and its shape. The venturi lumen may be formed using known machining methods or molding methods and may be formed of any acceptable materials, such as titanium or other hard materials suited to phacoemulsification surgery.

Thus, there has been shown an inventive phacoemulsification cannula for use in ophthalmic surgery, and especially cataract surgery, which provides increased suction at the distal end 18 as compared to prior art cannulas. This increased suction allows greater purchase of a cataract during surgery, which allows the surgeon to manipulate and hold the cataract with the phacoemulsification cannula and more efficiently break up and aspirate the cataract from the patient's eye. This increased purchase or holdability enhances the safety and efficiency of an operation by allowing a surgeon to more easily manipulate a cataract as compared to prior art surgery with a prior art cannula at the same aspiration level.

What is claimed:

1. A phacoemulsification cannula for use in ophthalmic surgery comprising:
    a hub for engagement with an ophthalmic surgical instrument;
    an elongated needle having a proximal end attached to the hub and a distal end;
    wherein the needle has an aspiration lumen with a first diameter spanning a majority of a length of the needle from the proximal end towards the distal end;
    wherein the needle has a venturi lumen formed from the distal end to the aspiration lumen, wherein the venturi lumen includes a first venturi section having a maximum diameter, and a second venturi section having a minimum diameter, and a third venturi section ending at a place connecting the aspiration lumen to the venturi lumen; and
    wherein the venturi lumen includes structure forming smoothly varying transitions between each of the first, second, and third venturi sections.

2. The cannula of claim 1, wherein the venturi lumen has a generally hour-glass shape.

3. The cannula of claim 1, wherein the venturi lumen includes structure creating a double-venturi.

4. The cannula of claim 1, wherein the minimum diameter of the second venturi section is approximately equal to the first diameter.

5. The cannula of claim 1, wherein the third venturi section has a largest diameter greater than the minimum diameter and equal to or less than the maximum diameter.

6. The cannula of claim 5, wherein the largest diameter of the third venturi section is equal to or greater than the first diameter.

* * * * *